United States Patent [19]
Silley et al.

[11] Patent Number: 5,861,305
[45] Date of Patent: Jan. 19, 1999

[54] ANAEROBIC CABINETS AND SYSTEMS

[75] Inventors: Peter Silley, Bingley; Donald Charles Whitley, Bradford; Evan Jonathan Kitsell, Silsden, all of England

[73] Assignee: Don Whitley Scientific Limited, Shipley, England

[21] Appl. No.: 817,324

[22] PCT Filed: Oct. 6, 1995

[86] PCT No.: PCT/GB95/02369

§ 371 Date: Jul. 1, 1997

§ 102(e) Date: Jul. 1, 1997

[87] PCT Pub. No.: WO96/11092

PCT Pub. Date: Apr. 18, 1996

[30] Foreign Application Priority Data

Oct. 8, 1994 [GB] United Kingdom .................... 9420333
Sep. 9, 1995 [GB] United Kingdom .................... 9518485

[51] Int. Cl.⁶ .................................................. C12M 3/00
[52] U.S. Cl. ................................. 435/286.6; 435/303.2; 312/1; 454/57; 600/22; 422/104
[58] Field of Search ................................. 312/1; 454/49, 454/51, 56, 57; 600/21, 22; 422/104; 435/286.6, 289.1, 303.1, 303.2

[56] References Cited

U.S. PATENT DOCUMENTS

| | | | |
|---|---|---|---|
| 3,536,370 | 10/1970 | Evans ........................................... | 312/1 |
| 4,111,753 | 9/1978 | Folsom .................................... | 195/126 |
| 4,262,091 | 4/1981 | Cox ......................................... | 435/253 |
| 4,336,329 | 6/1982 | Hesse ........................................... | 435/3 |
| 4,892,830 | 1/1990 | Findley et al. .......................... | 435/290 |
| 5,257,957 | 11/1993 | Diccianni et al. ........................ | 454/57 |
| 5,259,812 | 11/1993 | Kleinsek .................................. | 454/57 |
| 5,599,398 | 2/1997 | Lenglen ...................................... | 134/1 |

FOREIGN PATENT DOCUMENTS

| | | | |
|---|---|---|---|
| 0 168 915 A1 | 1/1986 | European Pat. Off. | ......... C12M 1/04 |
| 0 411 794 A1 | 2/1991 | European Pat. Off. | ......... C12M 1/00 |
| 1 186 485 | 8/1959 | France . | |
| 29 24 446 A1 | 6/1979 | Germany | ......... C12N 5/02 |
| 3/247666 A | 5/1991 | Japan . | |
| 2 174 714 | 11/1986 | United Kingdom | ............. C12M 1/00 |
| WO 94/22715 | 10/1994 | WIPO | ............... B65B 1/04 |

*Primary Examiner*—David A. Redding
*Attorney, Agent, or Firm*—Townsend and Townsend and Crew

[57] ABSTRACT

The invention provides an exemplary anaerobic cabinet system which comprises as least one anaerobic cabinet which defines an enclosure interior of which is visible from outside of the cabinet. The cabinet includes a mechanism for inducing and maintaining a prescribe low oxygen internal atmosphere within the enclosure. The cabinet further includes at least one hand/arm access port, a controlled lock-type access mechanism for manually introducing and removing items through the port, and a hand/arm access port provision which is operably coupled to the lock-type access mechanism for manipulating items within the cabinet. The lock-type access mechanism comprises a door provision which in combination with the port provision define an import chamber for loading and/or unloading items to and from the enclosure through the port.

20 Claims, 5 Drawing Sheets

ANAEROBIC CABINETS AND SYSTEMS

DESCRIPTION

This invention relates to anaerobic cabinets and systems such as used or intended for use in microbiology laboratories.

Requirements for anaerobic cabinets can vary widely according to the amount and types of work to be done at any particular location in relation to anaerobic organisms. It is customary for established manufacturers and suppliers of anaerobic cabinets, such as ourselves, to offer different sizes of cabinets, and appropriate variations of related facilities such as cabinet loading and unloading by way of means individual to each cabinet, also provision of access ports typically in pairs equipped with arm-tubes, whether arm-sealing for bare-hands use or as glove-tubes.

It is a general object of this invention to assist providing users of anaerobic cabinets with greater flexibility, versatility and economy of operating such cabinets, whether on an individual or on a more systematic basis.

Prior references drawn specifically to our attention include patent specifications U.S. Pat. No. 4,262,091 concerning filling petri dishes with culture medium in oxygen-free atmosphere of a central one of three anaerobic cabinets each having arm-tube manipulation access and communication passageways between them for empty petri dishes from left or right one of the anaerobic cabinets and filled petri dishes to right or left one of the anaerobic cabinets which can be separated from the communication provisions; EPA 411,794 concerning achieving low-hydrogen atmospheres in anaerobic cabinets by nitrogen and/or carbon dioxide to a standard gas mixture further including hydrogen, providing sealing bungs in ends of "bare-hands" type arm tubes, and providing nitrogen inflatable outer door seals for lock-type access provisions to one end of the main cabinet chamber; U.S. Pat. No. 4,111,753 concerning use of controlled anaerobic atmosphere transport units that dock with lock-type access provisions of anaerobic cabinets in bringing specimens for loading thereto and subsequent manipulation using gloved arm-tubes; and GB 2,174,714 for an anaerobic cabinet system having specimen entry from an end lock-type access unit to a main manipulation and thence to a compactly packed nurture chamber. Compared with such systems aspects and embodiments of this invention afford particular advantages, including relative to lock-type access provisions, particular at manipulation porting and/or shared by at least two cabinets.

According to a first aspect of this invention, there is provided an anaerobic cabinet or system in which each anaerobic cabinet comprises an enclosure with means for providing for all of visibility of its interior from outside, inducing and maintaining prescribed low-oxygen internal atmosphere, controlled lock-type access for manual introduction and removal of items, and hand/arm access port provision for manipulation of said items in the cabinet, the lock-type access including door provisions at least at said port provision affording an in-port chamber for loading and/or unloading appropriate items to and from the chamber through the port/door provisions.

According to a second aspect of this invention, there is provided an anaerobic cabinet or system in which each anaerobic cabinet comprises an enclosure with means for providing for all of visibility of its interior from outside, inducing and maintaining prescribed low-oxygen internal atmosphere, controlled lock-type access for manual introduction and removal of items, and hand/arm access port provision for manipulation of said items in the cabinet, the lock-type access comprising an access lock unit having first access provisions for said introduction/removal of items and other access provisions capable of individually servicing at least two cabinets each with its own cooperating cabinet access provisions relative to such then shared lock-type access unit.

Such a system is conveniently implemented as a central or medial lock provision between first and second cabinet extensions to left and right, respectively. Access to the system can be from front or rear of the shared or common access lock provision, usually the front, and cabinet access can be through left and right side walls, respectively, of the lock provision.

Each cabinet provision served by a common access lock provision can have its own atmosphere control system, including for temperature; and such control system could further serve the access lock provision wherever a match is required. Alternatively, perhaps preferably, atmosphere control for each cabinet may be by or from a common control system associated with common access lock provision. At least programmed microprocessor provisions will normally be so located. Moreover, even such common control system can usefully allow at least some differences between controlled cabinets, say at least as to temperature, maybe further as to one or more gas components or otherwise as to desired gas mixture. In any event, it is useful to have at least condensing means associated with each cabinet provision, say as a panel at the distal end of each.

The above but also other configurations are achievable using a systems approach based on modularity of constituent units that may have or afford other novel and advantageous structural features and/or association options and/or individual or combinational facilities.

According to another aspect of this invention, there is provided an entry/exit lock unit with atmosphere control means operable to achieve desired anaerobic gas conditions (from other conditions including open to ambient), both within itself and further through two selective access means for sealing or communicating separately to either side of the unit.

Such a lock unit is, of course, consistent with achieving a configuration as for the second aspect, but on a modular basis, namely flanking cabinet units serviced through left and right sides of the lock unit. As above, the lock unit can conveniently serving for system loading and unloading at its front, say via an up/down sliding or a door bottom hinged door to open by pulling down, usually to horizontal. The cabinet units can typically afford manipulation access by ports with arm-tubes, also from their fronts, and whether as glove-tubes or otherwise to afford a so-called "bare-hands" facility.

For at least one of ports equipped or to be equipped with arm-tubes, whether of said cabinet units or more generally, the first aspect of this invention concerns door provisions at said at least one port to afford a small chamber for loading and/or unloading appropriate items to and from the chamber. Such port chamber can extend from within an inner door, preferably hinged to open into the chamber, at least to (if not into) an arm-tube holder preferably itself hinged to give access to the port chamber from outside the cabinet.

Suitable seals for the inner door and/or the arm-tube holder can be as sharp edges onto resilient sealing material, typically registering localised circumscriptions of the door and/or holder, conveniently with closed ring-like seals on the door/holder and triangular generally knife-edge ring formations on opposite sides of cabinet/port walling. For the holder, say effectively a hinged door with a central aperture outwardly necked to take ends of arm-tubes, at least as equipped with such seals, applied pressure in the closed position is preferred, say by way of at least one biassed catch, say as an axially spring-loaded knob on the holder and for turning between engagement and disengagement of a fixed cooperating part associated with cabinet walling. For the inner door, at least as equipped with such seals, applied pressure in the closed position may be applied using a biassed final closure achieving mechanism, say a spring-loaded rotatable shaft carrying a door engager, conveniently with a reciprocal rotation drive externally triggerable to release the inner door by one direction of shaft rotation, conveniently involving (if required) first winding a biassing helical torsion spring to solid (mutual engagement of its turns), and operative automatically to finally close the inner door by the other direction of shaft rotation, conveniently involving a micro-switch after manual inner door movement most of the way to closure. At least inner door opening can be by a foot pedal and/or remote wire-less transmission, say of radio or infra red type. At least such inner door opening and pressurised closing provisions constitute another aspect of this invention.

If desired, and then generally advantageously, a satisfactory access regime for such a port chamber may involve atmosphere control provisions specific to the chamber, say for drawing a vaccuum, perhaps further for flushing with inert gas, such as nitrogen, and/or positively filling with anaerobic gas mixture matching contents of the cabinet), and related gas connection(s) thereto. In one such regime, provision is/are for drawing vacuum and for connecting to pressurised inert gas, say nitrogen, conveniently in that order, and whether as a single or repeated two-stage cycle. An addition, or alternative to inert gas (e.g. nitrogen) flushing, can usefully involve matching to the cabinet's anaerobic atmosphere, say by pumping therefrom or otherwise taking from supply thereto.

It helps, particularly as to diluting initial oxygen content with only one or two flushing cycles, where the volumes of glove-tubes are significantly greater than the volume of the port chambers at least as and when occupied by items to be loaded to the cabinet. Indeed, at least then, an alternative to positive flushing might even be by use of simple one-way valves for gas flow out to ambient from the glove-tube holder and gas flow in from the cabinet through the inner door, say in order to enable a sequence for manual flushing of the port chamber using the glove tube. This could be practical for high enough available anaerobic gas flow rates, and readily achieve below five percent oxygen for two flushes where the glove-tube volume is five or six times the unoccupied volume of the port chamber. Even lower oxygen levels can be produced if vaccuum is available at the port chambers, including even if the arm-tube volume is not very much greater than the port chamber volume.

Another aspect of this invention generally concerning cabinet ports for manipulation access using arm-tubes concerns the shape or configuration of each such port, which has hitherto having been generally circular, and specifically improvement represented by giving the ports an elongated configuration. When used along with the last preceding aspect, the port access chamber concerned can be bigger, for example enabling a stack of Petri dishes to be loaded or unloaded at the same time through a vertically elongated port. In any event, elongation of manipulation access ports can significantly improve ease of working within the cabinet, perhaps particularly for vertical elongation of both of a customary pair of ports equipped with arm-tubes. Compared with conventional circular ports, vertically elongated ports can have tops and bottoms curved much as before but with sides only slightly curved, thus to achieve desired improvements and retain capability for use of simple O-ring type seals.

It is envisaged that modularity further permit adjoinment of cabinet units end to end, so that a said access lock unit can be associated with series of two or more cabinet units to either or both sides. Generally matching aperturing provisions in sides of access lock units and in ends of cabinet units can be detailed to permit sealing with through access between cabinets or sealing with selective access between the lock and cabinet units or sealing to close off at either of one side of a lock unit or one end of a cabinet unit, whether using a condensing panel or otherwise.

A particularly advantageous condensing provision drains condensate to exterior of the cabinet unit and provides for its subsequent evaporation. A fan blowing ambient air against external cabinet walling is sufficient to induce adequate condensation internally on that walling, which can advantageously be thin thereat. Internal grooved ledging of cabinet walling can be in a V-shape to catch condensate for exit from the cabinet at the downward apex of the V-shape. Preferred condensate exit from the cabinet is controlled by a valve opened intermittently, say at regular intervals, such as for about twenty to thirty seconds every half hour or so. Suitable condensate evaporation can be by wicking action from a condensate receiver, say through a sheet or pad that could be laid over a support to present a main surface to ambient air, preferably with microbicidal action associated therewith, say as impregnation of wicking material.

In operation, preferred anaerobic cabinets hereof have small internal overpressure compared with external ambient, say up to about 12.5 mm water gauge, which can help use of arm-hole port accessing and/or valved condensate exit. Limiting of such internal overpressure can be by venting through a trap, preferably of suitable oil, advantageously with a non-return valve from the cabinet.

Features of such condensing and overpressure control provisions constitute other aspects of invention.

Another aspect of this invention concerns a basic anaerobic cabinet unit (of a modular system) connectable at either end to any one of at least another similar cabinet unit to operate in a satellite manner, and an access lock unit that may include control provisions for the cabinet unit concerned and other cabinet units, and a condenser panel.

It is further envisaged that a basic anaerobic cabinet unit be available as a minimum installation in a form that is usable without an access lock unit of the aforesaid modular system, then with some other access lock provision, which could be a smaller alternative lock provision at and through its end wall, or may well be no more than the port chamber provision(s) indicated above and for either or both of a pair of ports equipped with arm-tubes, then further preferably elongated as also indicated above. For such a minimum installation cabinet, all control electronics, together with electro-mechanical gas flow pumps and valves, will be directly associated with the basic cabinet unit, conveniently in an upper or header box located on and above the usable cabinet enclosure as such.

It is particularly preferred that basic anaerobic cabinets, whether for individual use as a minimum installation or for use in a multi-unit modular system hereof, be similar as to gas etc connections to their usable enclosures, with access thereto in such upper or header boxes. Then, the contents of such boxes will vary according to whether electronic etc control items are local or within a common control as indicated above from a lock unit of a modular system.

It is preferred that lower and upper cabinet parts, i.e. usable or working enclosure and header box, be with the front of the lower part sloping upwards and backwards and transparent at least above manipulation access ports, and the upper part sloping forwards and upwards from junction with the lower part to below a narrow front panel that will afford control system inputs/indicators for a minimum installation cabinet.

Specific implementation for practical embodiment if this invention in its various aspects will now be described, by way of example, with reference to the accompanying diagrammatic drawings, in which:

Figure 1:
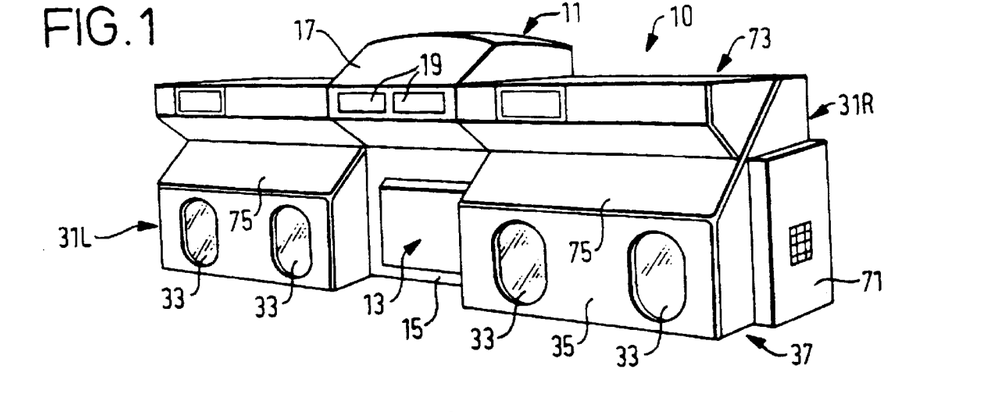
FIG. 1 is a perspective outline view of an anaerobic system or installation.

Referring first to FIG. 1, an anaerobic system or installation 10 with a central lock provision 11 flanked by two cabinet facilities 31L, 31R extending to left and right, respectively. The lock unit 11 has a front door 13 for loading and unloading items to and from the system 10. The door 13 will have convenient provisions for sealing and for opening and closing, which can be of a wholly known and conventional nature as to their detailing. Up/down sliding action is feasible for the door, and may be accompanied by rearward and forward first movements off and onto sealing provisions at start and end of opening and closing movements that are otherwise up and down. However, insetting of the lower part 15 of the lock unit relative to the flanking cabinet units 31A,B is perhaps particularly conducive to using a door 13 that is bottom hinged to open downwards and outwards, say to afford a pre-loading tray or first organising tray for items going in or coming out of the system 10.

Upper part 17 of the lock unit 11 is indicated with control panel provisions 19, and will serve to house control system parts that are common to the cabinet units 31L,R to either side. As mentioned above, it is readily made feasible for the control system, such as based on a programmed microprocessor, to control the left and right cabinets differently.

Figure 2:
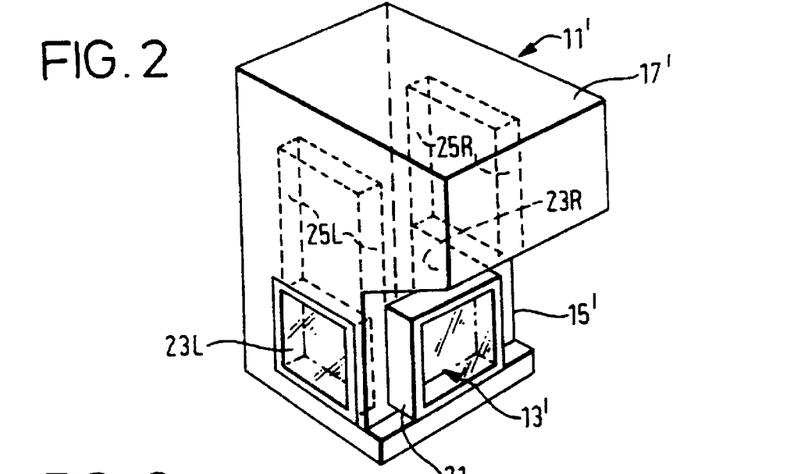
FIG. 2 is a perspective outline view of a lock unit to fit to either or both sides to a cabinet unit.

The lock unit will have suitable opening and sealingly closing communication provisions at both of its sides, i.e. separately relative to both of the cabinets 31L and 31R. Any satisfactory such provisions can be made. FIG. 2 using primed reference numerals and showing the system access door 13' on an outward porch formation 21, further indicating up/down sliding door systems see door outline indications 23L,R and side slide tracks/frames 25L,R. It will be appreciated that items requiring anaerobic conditions for investigation can go into and out of either of the cabinets 31L,R at will and as desired, including for spending some time in one and other time in the other between loading and unloading to the system 10 as a whole.

The door provisions (23L,R) of the lock unit 11 will, of course, be operable and normally operated from the cabinets 31L, using its customary access provisions for manipulation, typically using arm-tubes or sleeves connected at ports 33 usually provided in pairs, one for each hand/arm of a technician, and usually of a gloved type (unless a "barehands" facility is to be provided. FIG. 1 indicates such ports 33 in outline manner only (without arm/glove-tubes or sleeves) as holes through front wall 35 of lower part 37 of cabinets 31, but with elongation to aid manipulation via those ports 33. Vertical elongation is shown for both of a pair of ports for both of the cabinets 31L,R.

Figure 3:
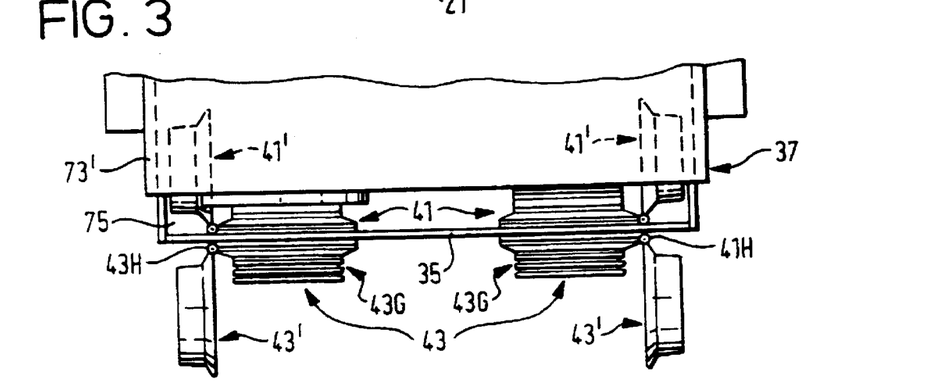
FIG. 3 is a fragmentary plan view of forward parts of a cabinet unit showing port access chambers.

FIG. 3 shows fitting to manipulation ports, such as outlined at 33 in FIG. 1, of an inner door 41 and an outer annular holder 43 for arm-tubes or sleeves (still not shown, but well known as fitting to grooving 43G), each hinged, see 41H and 43H, to open inwards and outwards, respectively, in both cases towards the sides or ends of the cabinets 31, see dashed indications and primed references 41' and 43', It is noted that inner doors 41' then tuck neatly away in the front corners of the cabinets 31, i.e. well clear of interfering with manipulative access through the ports 33 and without obstructing access relative to the lock unit 11 (or any further cabinet unit as will appear below).

Figure 4:
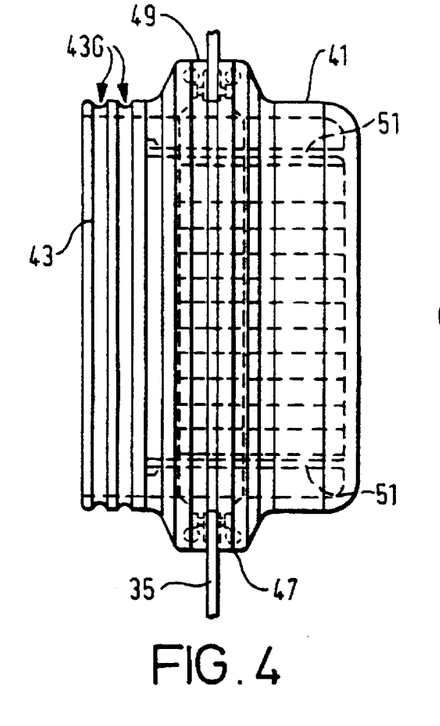
FIG. 4 is a detailed side elevation of port access chamber parts.
Figure 5:
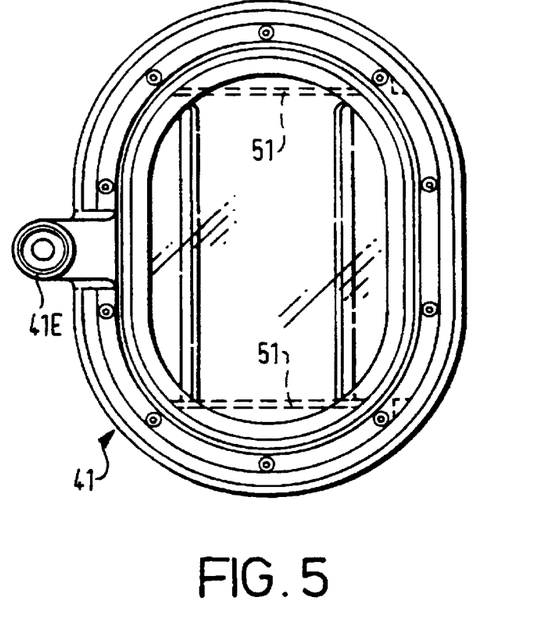
FIGS. 5 is a detailed front view of an inner door part of the port access chamber.

The elevational view of FIG. 4 is from the unhinged side of such port parts 41, 43, but shows greater detail including inner and outer fitting rings 47 and 49 that are fitted securely into front wall aperturing such as 33. Also clearly apparent is the substantial depth of the inner door 41, together with indications 51 of shelf provisions interiorly near top and bottom of the inner door part 41. The depth of the inner door 41 and the extent of the shelf provisions 51 should be consistent with loading Petri dishes of useful size. Elongation of the inner door 41 to match elongation of the ports 33 intendedly to ease/aid manipulation now further serves to improve capacity of the in-port chamber bounded by the shelves 51, say so as to take a stack of Petri dishes. FIG. 5 also shows the shelves 51, but omits hinge leaving.

Figure 6A:
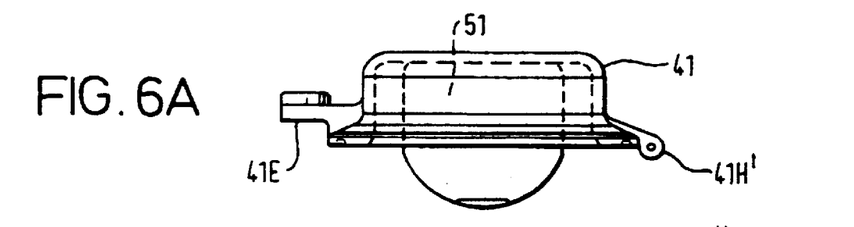
FIGS. 6A–D are views from above of separated parts of the port access chamber.
Figure 6B:
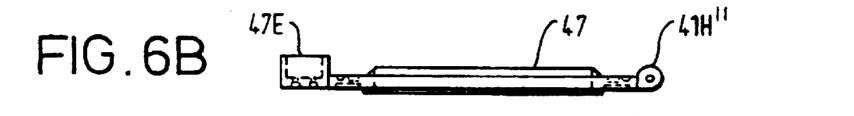
Figure 6C:
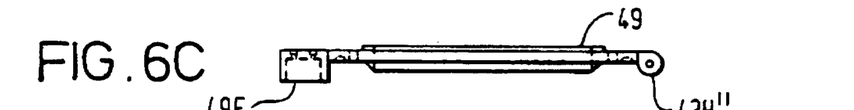
Figure 6D:
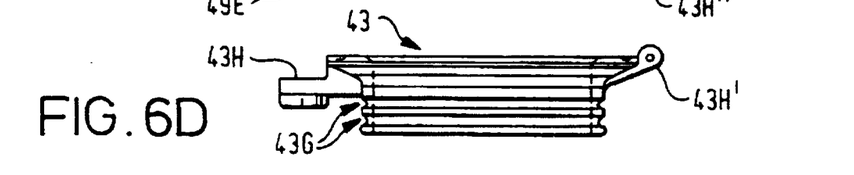

Yet further detail in the effectively exploded view represented by FIGS. 6A–D, includes protruding ring formations to each side of the fitting rings 47 and 49 to assist in achieving required sealing relative to either side of the front wall 35 on the one hand and with the inner door 41 and the arm-tube holder 43 on the other hand. Also shown are cooperating pairs of hinging leaves 41H' with 41H" and 43H' with 43H"; along with other side extensions subscripted "E" to cooperate as releasable securements, specifically 41E with 47E and 43E with 49E, and whether of a wholly manual mechanical or at least partly electrical/magnetic and maybe automatic type. FIG. 6A further shows rounded extension 51E and lipping 51L of the shelves 51 to aid both of item support partly within the arm-tube holder 43 and gripping to swing the inner door 41 back to the aperture 33 whenever so required.

In operation of the port chambers as indicated hereinbefore, the inner door 41 will first be loaded with any items to be taken out of the cabinet 31 to ambient and then closed by a technician, in each case using the arm tube of the corresponding holder 43. Then, that holder 43 will be swung away and the bottom one of the shelves 51 will be unloaded (if items are being removed) then loaded with any items to go directly into the cabinet 31 (i.e. rather than go through any lock unit 11).

The port chamber parts, perhaps preferably one of the fitting rings 47, 49, may have at least a vaccuum drawing connection to take most ambient, normally oxygen-rich, atmosphere out of the port chamber. Opening a valve (not shown) from the cabinet, say through the inner door 41, along with normal continuation of anaerobic atmosphere supply to the cabinet 41 could, if there is enough anaerobic gas flow available, flood the port chamber and arm tube, thus producing a very low oxygen content. That low oxygen content could be further diluted by another cycle of vaccuum and flooding from the cabinet; and might be repeated as often as desired or required. However, it may well be sufficient, at least where the arm-tube volume is large compared with empty volume of the port chamber, to provide only one-way valves (specifically from the port chamber to ambient and from the cabinet into the port chamber) and use the arm-tube as a pump, at least if closed off by glove provision.

Alternatives could involve the alternate use of drawing vaccuum and making connection to pressurised inert gas, usually nitrogen available as a component of preferred or normal anaerobic cabinet working atmospheres, and/or pumping actual anaerobic atmosphere into the port chamber between or at least after the last of vaccuum applications.

Whilst FIG. 1 can be for a purpose-built system of a central lock 11 and flanking cabinets 31L,R, it could equally well represent three units of a modular system (of which the lock of FIG. 2 could be one unit). In any event, addition of further cabinet units (like 31) end-to-end with either of the left-hand or right-hand cabinet shown (31L or 31R) would be useful. One way of doing this is indicated in FIG. 7 showing another cabinet 31X for adjoinment with the left-hand cabinet 31L of FIG. 1.

Figure 7:
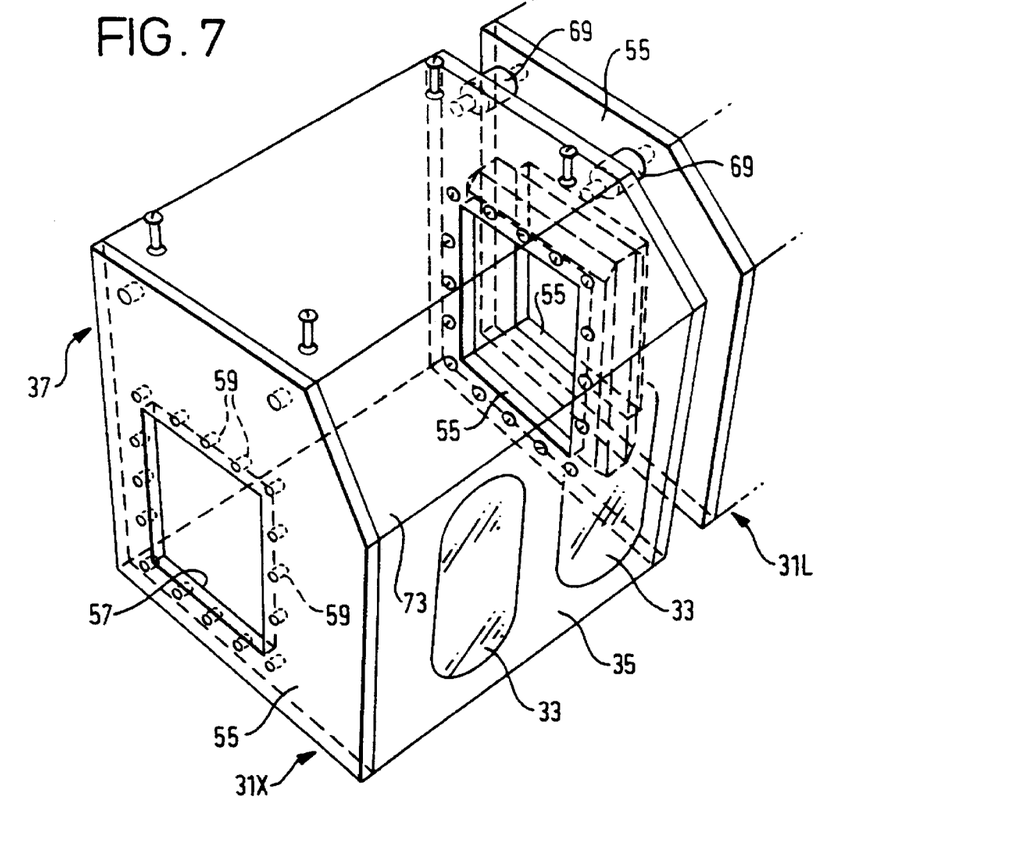
FIG. 7 is a perspective view of adjoinment between two cabinet units end-to-end.
Figures 7A, 7B:
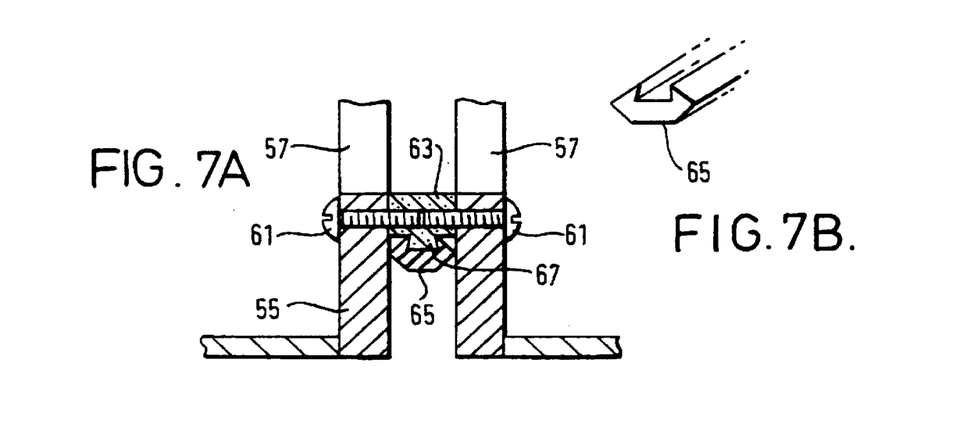
FIG. 7A shows a related sealing detail.

In FIG. 7, side or end walls 55 of the lower parts 37 of the cabinets 31X and 31L have apertures 57, shown as square (but not necessarily so); and spaced connection bolt holes 59 are shown about them. Sealed interconnection or adjoinment is shown provided (see also FIG. 7A) by bolts 61 screwing into a frame of structural foam strip 63 shown with an exterior seal 65 as an extrusion of softer elastomeric material conveniently made into an effectively continuous loop and snapped over a key formation 67 of the foam strip 63 (also conveniently an extrusion, of course). The seal strip 65 will, of course, be compressed by the side/end walls 55 of the cabinets 31X,L. Extra connection bolt provisions are also indicated at 69 for maximising structural integrity and stability.

Figure 8A:
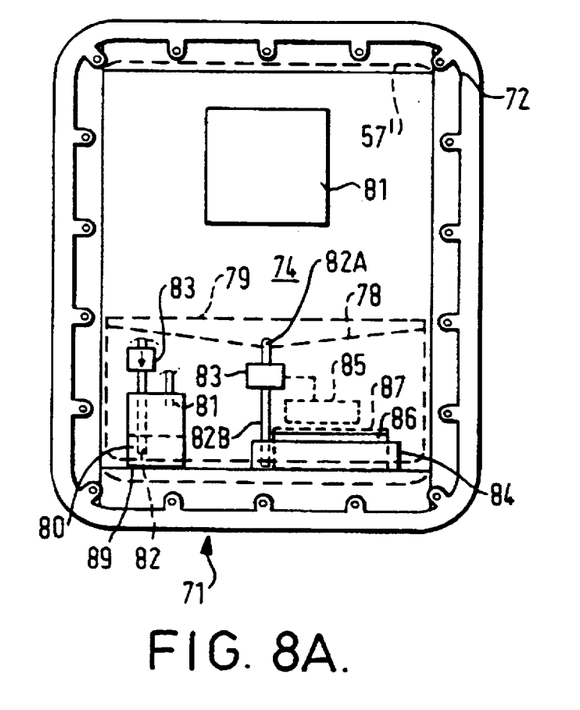
FIG. 8 shows a condenser panel unit in exterior plan and sectional views.
Figure 8B:
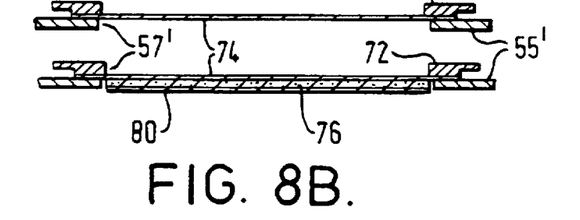
Figure 8C:
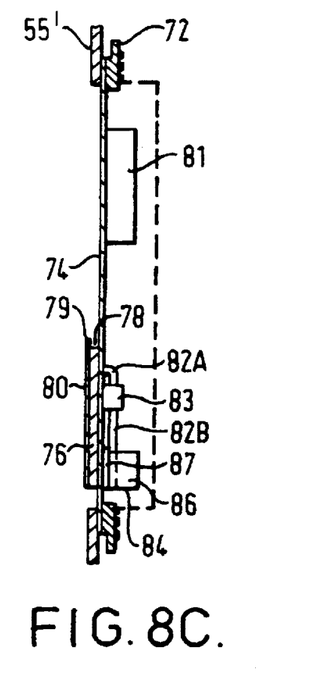

For our modular system, it is preferred that the apertures 57 be the same regardless of whether joining to a lock unit or to another cabinet unit or, indeed, to a cabinet closure such as a condenser unit as indicated at 71 in FIG. 1, and further in FIG. 8. Specifically, in the latter, unit 71' comprises a flanged frame 72 fitting about aperture 57' in cabinet end wall 55' and carrying a thin plate or sheet 74 with thicker interior insulation 76 at its lower part presenting a V-bottom groove 78 from its upper edge 79 shown defined by further sheet or plate 80. A fan 81 fitted (mounting provisions and other details omitted for clarity) to blow ambient air onto an upper part of the sheet or plate 74 and cause condensation on the inner surface of the latter. Condensate will collect in the V-grooving 78 for exit through an aperture at its downward apex into a tube part 82A to valve 83 controlling onward flow through tube part 82B to evaporator provision 84. To assist in avoiding unwanted effective venting or other interior atmosphere problems, the valve is operated by a timer 85 (shown dashed as normally in control electronics) on an intermittent basis, say opened for twenty seconds every half hour (not critical), otherwise closed. Suitable evaporation provision is shown by way of condensate receptacle 84 with upstanding inverted-V support 86 for wicking material 87 shown in sheet form laid on the support 86 with its edges to dip into in condensate. A microbicide impregnated into the wicking material 87 is preferred. It is further convenient for the condensing unit 71' to house at its lower part within outer grille cover provision 88 a liquid, preferably oil, trap access 89 to ambient. This provision is shown as a bottle containing oil 180, and with outlet tube 181 to ambient atmosphere, and inlet tube 182 from the cabinet concerned into the liquid 180 via one-way valve 183, preferably settable or otherwise controllable for opening at a particular overpressure in the cabinet, say about 12 mm water gauge.

Figures 9, 9A:
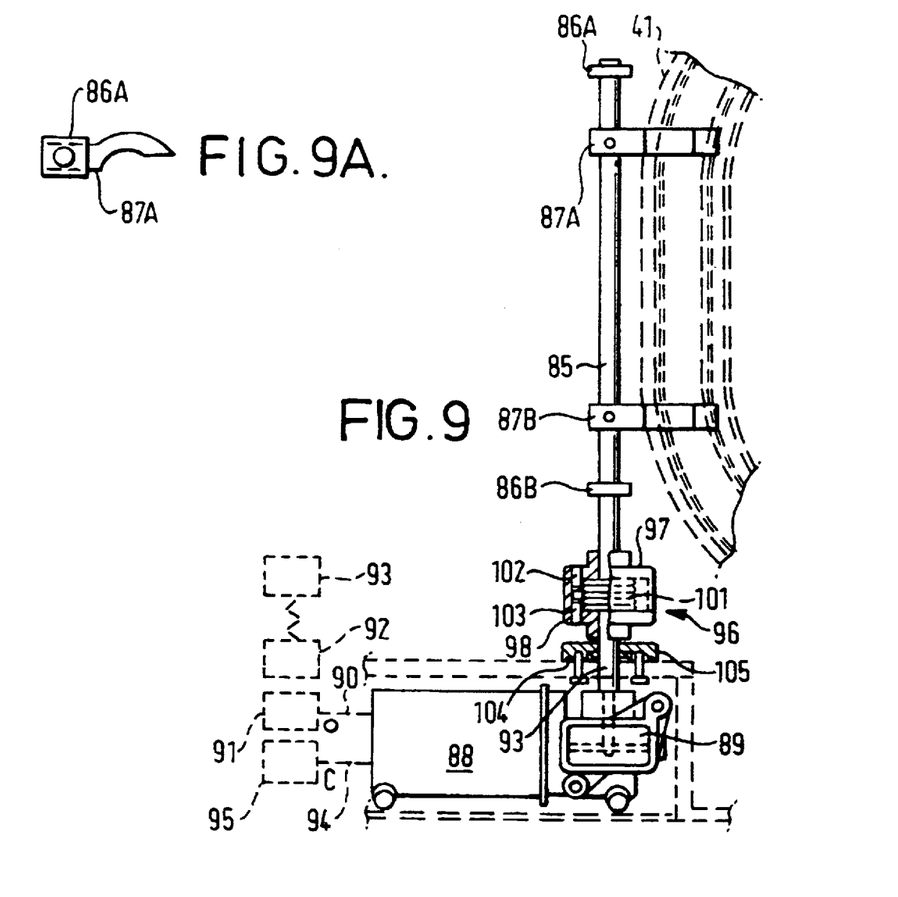
FIG. 9 shows opening and closing provision for an inner arm-tube port in front part-sectional and top end views.

Particularly preferred opening and closing provisions for the inner port/lock doors 41 is shown in FIG. 9, by way of a two-way part-turn-rotational shaft 85 running in bearings 86A, 86B and carrying spaced door engagers 87A and 87B. The shaft 85 is shown driven by motor 88 through coupling 89 very much in the manner of a motor windscreen wiper, but with individual control of each direction, say opening on line 90 by a signal from a foot pedal 91 or from a receiver 92 for a remote radio or infra-red transmitter 93, and for final stage of closing by a signal on line 94 from a micro-switch 95 engaged by the door 41 in being partly, preferably mostly, closed manually. The drive is shown applied to shaft 85 by a biassing-to-closed provision 96, advantageously two coupling parts 97 and 98 associated irrotationally with the shaft 85 and motor driven shaft 99, respectively. Coupling part 97 is shown cup-shaped to house helical torsion spring 101, which acts to apply bias between studs 102 and 103 fixed to the coupling parts 97 and 98, respectively. Opening rotation can include a first part to take up any slack in the spring 101, then drive the shaft 85 with the spring turns touching or solid. The motor 88 and its output drive coupling 89 are indicated outside the cabinet, conveniently below, and shaft 89 is shown with a seal 104 and seal clamping holder 105.

Figure 10:
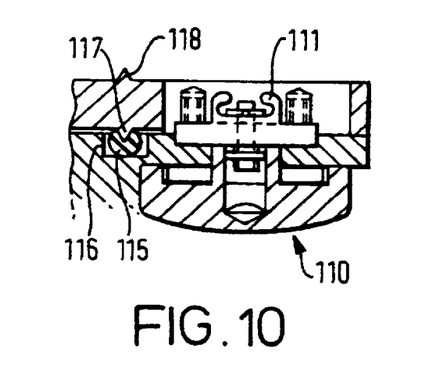
FIG. 10 shows door sealing and arm-tube holder closing provisions mostly in section.

FIG. 10 shows a manually operated pressure clamp 110 for the outer doors or arm-tube holders 43. This is conveniently of well-known cam-action type acting relative to front provisions of the cabinet, further preferably with sealing provisions 111 . Further preferred door or holder 43 seal provisions are indicated by way of circumscribing O-ring 115 in groove 116 and knife edge formation 117 of the cabinet front. Similar interior seal provision for the inner door 41 is also indicated by interior knife edge formation 118.

Further in relation to our preferred modular system, units as illustrated can readily conform with what has been mentioned earlier herein, for example as to contents of upper parts or header boxes 73 of the cabinet units, also as to rearward and upward sloping of transparent fronts of the lower parts 37 of the cabinet units at 75 above the ports 33 to join with upward and forward sloping of the upper parts or header boxes 73 below control panel etc fascia walling, and further with lock units 11 extending higher but otherwise harmonising.

It will be appreciated that modularity of systems hereof is to extend as far as feasible through component parts, for example in avoiding "handing" of items such as the door/tube holder/fitting ring components of the port chambers.

We claim:

1. Anaerobic cabinet system comprising:
at least one anaerobic cabinet which defines an enclosure with an interior which is visible from outside the cabinet, the cabinet including means for inducing and maintaining a prescribed low-oxygen internal atmosphere within the enclosure, at least one controlled lock-type access mechanism for manual introduction and removal of items, at least one hand/access port to allow for manipulation of said items in the cabinet, and a hand/arm access port provision operably coupled to said lock-type access mechanism, said lock-type access mechanism comprising a door provision which in combination with said port provision define an in-port chamber for loading and/or unloading appropriate items to and from the enclosure through the port.

2. Anaerobic cabinet system according to claim 1, wherein the door provision comprises an inner door that is movable in the enclosure, the inner door being movable out of and back into sealed relation with the cabinet, wherein the lock-type access mechanism further comprises an arm tube holder to which the hand/arm access port provision is coupled, wherein the arm-tube holder is movable relative to the cabinet to allow access to the enclosure from outside of the cabinet by moving the arm-tube holder out of a sealing arrangement with the cabinet.

3. Anaerobic cabinet system according to claim 2, wherein said inner door and said arm-tube holder are each hinged to the cabinet to open into and away from the cabinet, respectively.

4. Anaerobic cabinet system according to claim 3, wherein said inner door and said arm-tube holder are biased into sealing relation with the cabinet.

5. Anaerobic cabinet system according to claim 4, wherein the inner door has applied bias pressure in the closed position by a final closure achieving mechanism comprising a spring-loaded reciprocally rotatable shaft carrying a door engager operative to release the inner door by one direction of shaft rotation, and operative automatically to finally close the inner door by the other direction of shaft rotation on operation of a micro-switch after manual inner door movement towards closure.

6. Anaerobic cabinet system according to claim 2, further comprising seals for said inner door and said arm-tube holder, wherein the seals each comprise a resilient sealing strip which engage sharp edges of respective cabinet beads circumscribing said port.

7. Anaerobic cabinet system as in claim 1, further comprising a plurality of anaerobic cabinets.

8. Anaerobic cabinet system comprising:
at least two anaerobic cabinet units which each define an enclosure with an interior which is visible from outside the cabinet units, wherein each cabinet unit includes a cabinet access provision, and wherein at least one of the cabinet units includes a hand/arm access port provision for manipulation of items in said cabinet unit;
means for inducing and maintaining a prescribed low-oxygen internal atmosphere within the cabinet units;
a controlled lock-type access means for manual introduction and removal of items to and from the cabinet, wherein the lock-type access means is coupled to the cabinet units and comprises an access lock unit having first access provisions for introduction or removal of items to or from the access lock unit and other access provisions which are adapted to interface with the cabinet access provisions to allow the cabinet units to be serviced through the access lock unit.

9. Anaerobic cabinet system according to claim 8, wherein the access lock unit includes control means operative for establishing and maintaining the same or differing parameters of atmospheres in and for each of said two cabinet units sharing the access lock unit.

10. Anaerobic cabinet system according to claim 8, wherein the access lock unit is between first and second cabinet units extending to left and right, respectively, with access to the cabinet system through a front wall of the access lock unit and with subsequent cabinet unit access through left and right side walls of the access lock unit.

11. Anaerobic cabinet system according to claim 8, wherein the cabinet units have side wall provisions alternatively accommodating through-access to said access lock unit or to another cabinet unit or a condensing unit or a blanking plate.

12. Anaerobic cabinet system according to claim 8, wherein a condensing unit which is adapted to fit in a side wall of one of the cabinet units comprises a panel with associated means for draining condensate to an exterior of the cabinet unit and for its subsequent evaporation.

13. Anaerobic cabinet system according to claim 12, wherein the associated means of the condensing unit includes a fan to blow ambient air against thin walling of the panel, internal grooved ledging of the panel in a V-shape to catch condensate for exit from the cabinet unit at the downward apex of the V-shape.

14. Anaerobic cabinet system according to claim 12, wherein the associated means of the condensing unit includes a valve opened intermittently to control exit of condensate from the cabinet unit.

15. Anaerobic cabinet system according to claim 12, wherein the associated means of the condensing unit includes an external condensate receiver and means for wicking condensate for evaporation into ambient air.

16. Anaerobic cabinet system according to claim 8, wherein the hand/arm access ports are adapted to receive arm-tubes and have an elongated or oval shape or configuration.

17. Anaerobic cabinet system according to claim 8, further comprising limiting means for desired internal over-pressure by venting from one of the cabinet units through a no-return valve and a trap.

18. Anaerobic cabinet system as in claim 17, wherein the trap comprises oil.

19. A controlled atmosphere cabinet system comprising:
at least one cabinet which defines an enclosure with an interior which is visible from outside the cabinet;
means for inducing and maintaining a prescribed low-oxygen internal atmosphere within the enclosure;
at least one hand/arm access port to provide access into the enclosure and to allow for manipulation of items within the enclosure;
at least one controlled lock-type access mechanism for manual introduction and removal of items through the port; and
a hand/arm access port provision operably coupled to the lock-type access mechanism, said lock-type access mechanism further comprising a door disposed in the enclosure which in combination with said port provision define an in-port chamber for loading and/or unloading appropriate items to and from the enclosure through the port.

20. Anaerobic cabinet system comprising:

at least two anaerobic cabinet units which each define an enclosure with an interior which is visible from outside the cabinet units, wherein each cabinet unit includes a cabinet access provision, and wherein at least one of the cabinet units includes a hand/arm access port provision for manipulation of items in said cabinet unit;

means for inducing and maintaining a prescribed low-oxygen internal atmosphere within the cabinet units;

a controlled lock-type access means for manual introduction and removal of items to and from the interior, wherein the lock-type access means is coupled to the cabinet units and comprises an access lock unit having first access provisions for introduction or removal of items to or from the access lock unit and other access provisions which are adapted to interface with the cabinet access provisions to allow the cabinet units to be serviced through the access lock unit; and wherein the access lock unit includes control means operative for establishing and maintaining the same or differing parameters of atmospheres in and for each of said two cabinet units sharing the access lock unit.

* * * * *